United States Patent [19]

North

[11] 4,287,374

[45] Sep. 1, 1981

[54] PROCESS FOR THE PRODUCTION OF FLUORONITROBENZENES

[75] Inventor: Robert A. North, Nottingham, England

[73] Assignee: The Boots Company, Nottingham, England

[21] Appl. No.: 80,616

[22] Filed: Oct. 1, 1979

[30] Foreign Application Priority Data

Oct. 5, 1978 [GB] United Kingdom ............... 39512/78

[51] Int. Cl.³ .............................................. C07C 79/12
[52] U.S. Cl. ................................... 568/937; 568/933; 568/938
[58] Field of Search ........................ 568/937, 933, 938

[56] References Cited

U.S. PATENT DOCUMENTS

| | | |
|---|---|---|
| 3,064,058 | 11/1962 | Duesel et al. .................. 568/937 |
| 3,240,824 | 3/1966 | Boudakian et al. ................ 568/937 |
| 3,480,667 | 11/1969 | Siegart et al. .................... 568/937 |
| 4,069,262 | 1/1978 | Kunz .............................. 568/937 |
| 4,140,719 | 2/1979 | Tull et al. ........................ 568/937 |
| 4,164,517 | 8/1979 | Fuller ............................. 568/938 |
| 4,226,811 | 10/1980 | Oeser et al. ..................... 568/937 |
| 4,229,365 | 10/1980 | Oeser et al. ..................... 568/937 |

FOREIGN PATENT DOCUMENTS

| | | |
|---|---|---|
| 2527944 | 1/1976 | Fed. Rep. of Germany ........... 568/937 |
| 2724645 | 12/1977 | Fed. Rep. of Germany ........... 568/937 |
| 1360327 | 7/1974 | United Kingdom .................. 568/937 |

*Primary Examiner*—Teddy S. Gron
*Attorney, Agent, or Firm*—Lawrence Rosen

[57] ABSTRACT

A fluoronitrobenzene is prepared by heating a mono chloronitrobenzene with an alkali metal fluoride and a phase transfer catalyst at a temperature of no more than 200° C.

13 Claims, No Drawings

PROCESS FOR THE PRODUCTION OF FLUORONITROBENZENES

This invention relates to a process for the production of fluoronitrobenzenes which are useful as intermediates in the production of certain pharmaceutical and agrochemical products.

British Pat. No. 1,469,700 describes the production of 2-fluoronitrobenzene in which 2-chloronitrobenzene is heated with an alkali metal fluoride at a temperature of 230°–250° C. in the presence of sulpholane. It is preferred for the ratio of sulpholane to 2-chloronitrobenzene to be from 0.30:1 to 0.90:1.

U.S. Pat. No. 4,069,262 describes a process for the preparation of 2-fluoronitrobenzene which comprises heating a mixture of 2-chloronitrobenzene, potassium fluoride of particle size 1–20 microns, and a catalyst in sulpholane for 2–8 hours at 240°–250° C. wherein the molar ratio of 2-chloronitrobenzene to potassium fluoride to sulpholane is 1:1–1.5:0.3–1.0.

In U.S. Pat. No. 4,140,719 there is described a method of preparing 2,4-difluoroaniline by reacting 2,4,5-trichloronitrobenzene with a fluorinating agent in the presence of a solid-liquid phase interface, the liquid phase comprising an organic solvent for the 2,4,5-trichloronitrobenzene, whereby 2,4-difluoro-5-chloronitrobenzene is formed which is then hydrogenated to reduce the nitro group and remove the chlorine atom to give the desired aniline. The presence of the chlorine in the 5 position activates the remaining chlorine atoms and enables the fluorination to proceed at temperatures around 100° C.

We have now surprisingly found that monochloronitrobenzenes and particularly 2-chloronitrobenzene (which of course contain no activating extra chlorine atom) can be fluorinated by using the low temperature described in U.S. Pat. No. 4,140,719.

We have also found by operating at these temperatures, which are below those described in British Pat. No. 1,469,700 and U.S. Pat. No. 4,069,262 that improved yields of fluoronitrobenzenes may be obtained and that corrosion of reaction vessels is generally reduced.

Thus the present invention provides a process for the production of a monofluoronitrobenzene in which a monochloronitrobenzene is heated with an alkali metal fluoride and a phase transfer catalyst at a temperature of no more than 200° C.

Such phase transfer catalysts are described, for example, in Angew. Chem. Internat. Edit. 13 (1974) No. 3 170; and J. Amer. Chem. Soc. 1971, 93, 195 and are usually quaternary ammonium or phosphonium compounds. Examples of such catalysts which may be used include long chain alkylammonium halides, e.g. tetradecyltrimethylammonium bromide; aralkylammonium compounds e.g. benzyltriethylammonium chloride or hydroxide and alkylphosphonium halides, e.g. hexadecyltributylphosphonium bromide.

Another feature of the present invention is that it is not necessary to use a solvent since similar yields are obtained both with and without a solvent. Should the use of a solvent be required then the present invention can be operated using commonly available organic polar aprotic solvents, e.g. dimethylsulphoxide dimethylformamide or sulpholane.

Preferably the alkali metal salt is potassium fluoride especially potassium fluoride in a finely divided state which contains less than 0.2% by weight of water.

Preferably the temperature of the heating is in the range 125°–170° C., especially 140°–150° C. Generally the heating is maintained for a period of 6–36 hours.

Preferably the molar ratio of catalyst to chloronitrobenzene is less than 1:10, especially from 1:50 to 1:15.

The fluoronitrobenzene and unchanged chloronitrobenzene may be recovered by standard procedures e.g. by steam distillation and fractionally distilling the resulting organic phase. An alternative method is to allow the mixture to cool, filter (adding toluene to assist filtration), distilling the toluene, and then finally distilling the residue.

The invention is illustrated in the following examples in which percentages are by weight unless stated otherwise and temperatures are in "°C".

EXAMPLE 1

Potassium fluoride (water content 0.2%) (69.6 g; 1.2 mole) and tetradecyltrimethylammonium bromide (18 g; 0.055 mole) were added to molten 2-chloronitrobenzene (157.5 g; 1 mole) with stirring. The mixture was heated to 140° C. for 28 hours. The reaction mixture was then allowed to cool to c. 100° C. and was filtered with the assistance of added toluene. The toluene was distilled and the residue was finally distilled in high vacuum to give 2-fluoronitrobenzene in 78% yield together with 5% recovered 2-chloronitrobenzene.

EXAMPLE 2

Potassium fluoride (69.6 g; 1.2 mole) and benzyltriethylammonium chloride (10.7 g; 0.05 mole) were added to molten 2-chloronitrobenzene (157.5 g; 1.0 mole). After stirring at 140° C. for 28 hours and a similar work-up to Example 1, 2-fluoronitrobenzene was obtained in 41% yield together with 7% recovered 2-chloronitrobenzene.

EXAMPLE 3

Example 1 was repeated using 4-chloronitrobenzene to give 4-fluoronitrobenzene in 60% yield together with 20% recovered 4-chloronitrobenzene.

EXAMPLE 4

Example 1 was repeated using dimethylformamide as a solvent. After stirring at 140° C. for 25 hours 2-fluoronitrobenzene was obtained in 67% yield, together with 15% recovered 2-chloronitrobenzene.

EXAMPLE 5

Example 1 was repeated using dimethyl sulphoxide as a solvent. After stirring at 140° C. for 24 hours 2-fluoronitrobenzene was obtained in 42% yield together with 28% recovered 2-chloronitrobenzene.

EXAMPLE 6

Example 1 was repeated with the molar ratio of catalyst to 2-chloronitrobenzene of 1:10 and using sulpholane as a solvent. After stirring at 150° C. for 17 hours 2-fluoronitrobenzene was obtained in 70% yield together with 13% recovered 2-chloronitrobenzene.

EXAMPLE 7

Potassium fluoride (69.6 g; 1.2 mole) and hexadecyltributylphosphonium bromide (25.2 g; 0.04 mole) were added to molten 2-chloronitrobenzene (157.5 g; 1 mole).

After stirring at 145° C. for 24 hours and a similar work-up to Example 1, 2-fluoronitrobenzene was obtained in 91.2% yield together with 2.4% recovered 2-chloronitrobenzene.

EXAMPLE 8

Potassium fluoride (244 g; 4.2 moles) and tetradecyltrimethylammonium bromide (67.2 g; 0.2 moles) were added to molten 2-chloronitrobenzene (630 g; 4.0 moles). After stirring at 145° C. for 28 hours and a similar work-up to Example 1, 2-fluoronitrobenzene was obtained in 89.2% yield, together with 4.1% recovered 2-chloronitrobenzene. Corrosion tests carried out during this reaction indicated negligible attack on stainless steel or glass enamel test pieces and very low corrosion rate on mild steel test pieces. In comparison when this reaction was carried out at 240° C. severe corrosion of the test pieces occurred.

EXAMPLE 9

Potassium fluoride (69.6 g; 1.2 mole) and undecyltributylammonium bromide (25.2 g; 0.06 mole) were added to molten 2-chloronitrobenzene (157.5 g; 1.0 mole). After stirring at 145° C. for 24 hours and a similar work-up to Example 1, 2-fluoronitrobenzene was obtained in 84.6% yield, together with 0.4% nitrobenzene.

COMPARATIVE EXAMPLE 1

Example 1 was repeated in the absence of the phase transfer catalyst to give 2-fluoronitrobenzene in 0.2% yield, together with 91% recovered 2-chloronitrobenzene.

COMPARATIVE EXAMPLE 2

Example 6 was repeated at a temperature of 220° C. After stirring for 11½ hours 2-fluoronitrobenzene was obtained in 18% yield together with 13% recovered 2-chloronitrobenzene.

COMPARATIVE EXAMPLE 3

Example 6 was repeated at a temperature of 240° C. After stirring for 17 hours, 2-fluoronitrobenzene was obtained in 4% yield together with 3% nitrobenzene and 33% 2-chloronitrobenzene.

COMPARATIVE EXAMPLE 4

A mixture of potassium fluoride (61.5 g; 1.06 mole), 2-chloronitrobenzene (157.5 g; 1.0 mole) and sulpholane (88.8 g; 0.74 mole) was heated to 140° C. for 28 hours. 2-Fluoronitrobenzene was obtained in 16% yield together with 61% recovered 2-chloronitrobenzene.

The poor yields in comparative Examples 1 and 4 illustrate the need for a phase transfer catalyst, whilst the poor yields in Examples 2 and 3 illustrate the disadvantage of operating at high temperature.

I claim:

1. A process for the production of a mono fluoronitrobenzene in which a mono chloronitrobenzene is heated with an alkali metal fluoride and a phase transfer catalyst at a temperature of no more than 200° C.

2. A process as claimed in claim 1 wherein the monochloronitrobenzene is 2-chloronitrobenzene.

3. A process as claimed in claim 1 or claim 2 wherein the alkali metal fluoride is potassium fluoride.

4. A process as claimed in claim 1, wherein the catalyst is a tetraalkylammonium salt.

5. A process as claimed in claim 4 wherein the catalyst is tetradecyltrimethylammonium bromide.

6. A process as claimed in claim 1 wherein the heating is maintained for a period of 6-36 hours.

7. A process as claimed in claim 1 wherein the reaction temperature is 125°-170° C.

8. A process as claimed in claim 7 wherein the reaction temperature is 140°-150° C.

9. A process as claimed in claim 1 wherein the molar ratio of catalyst to chloronitrobenzene is equal to or less than 1:10.

10. A process as claimed in claim 9 wherein the molar ratio of catalyst to chloronitrobenzene is from 1:50-1:15.

11. A process as claimed in claim 1 wherein the alkali metal fluoride is in a finely divided state.

12. A process as claimed in claim 1 wherein the alkali metal fluoride initially contains less than 0.2% by weight water.

13. A process as claimed in claim 1 wherein the reaction is conducted in the absence of a solvent.

* * * * *